United States Patent
Oshiki et al.

(10) Patent No.: US 8,355,775 B2
(45) Date of Patent: Jan. 15, 2013

(54) IMAGE DIAGNOSING SUPPORT METHOD AND IMAGE DIAGNOSING SUPPORT APPARATUS

(75) Inventors: Mitsuhiro Oshiki, Tokyo (JP); Ryuichi Shinomura, Higashimatsuyama (JP)

(73) Assignee: Hitachi Medical Corporation, Tokyo (JP)

( * ) Notice: Subject to any disclaimer, the term of this patent is extended or adjusted under 35 U.S.C. 154(b) by 899 days.

(21) Appl. No.: 11/628,404

(22) PCT Filed: May 30, 2005

(86) PCT No.: PCT/JP2005/009863
§ 371 (c)(1),
(2), (4) Date: Dec. 4, 2006

(87) PCT Pub. No.: WO2005/117712
PCT Pub. Date: Dec. 15, 2005

(65) Prior Publication Data
US 2007/0244393 A1    Oct. 18, 2007

(30) Foreign Application Priority Data

Jun. 3, 2004  (JP) ................................. 2004-165427
Jul. 30, 2004  (JP) ................................. 2004-222713

(51) Int. Cl.
*A61B 5/05* (2006.01)
(52) U.S. Cl. ........ 600/425; 600/407; 382/131; 382/154; 382/294
(58) Field of Classification Search .................. 600/407, 600/425; 382/131, 154, 294
See application file for complete search history.

(56) References Cited

U.S. PATENT DOCUMENTS 5,239,591 A *  8/1993  Ranganath ..................... 382/128
5,357,550 A    10/1994  Asahina et al.
(Continued)

FOREIGN PATENT DOCUMENTS
JP        58-019240        2/1983
(Continued)

OTHER PUBLICATIONS

M. Nakamura, et al., "6) Kekkannai Echo-ho", clinical Testing Zokango, Oct. 30, 2001, vol. 45, No. 11, pp. 1321-1325.

*Primary Examiner* — Brian Casler
*Assistant Examiner* — Joseph M Santos
(74) *Attorney, Agent, or Firm* — Antonelli, Terry, Stout & Kraus, LLP.

(57) ABSTRACT

This is an image diagnosing support method comprising: an acquisition step of acquiring a plurality of images obtained by imaging the same region of the same object with one or more medical imaging apparatuses and having positional information at the time each of the images was picked up; a selecting step of selecting a first image and a second image out of the plurality of images; a displaying step of displaying the first image and the second image; a step of designating one or more of first reference points on the first image; a step of figuring out second reference points, on the second image, each matching one or another of the first reference points; a first step of extracting for each of the first reference points a first region containing that point within it; and a second step of extracting for each of the second reference points a second region containing that point within it, characterized in that either one of the first step and the second step is performed earlier or both are at the same time.

22 Claims, 13 Drawing Sheets

U.S. PATENT DOCUMENTS

| | | | | |
|---|---|---|---|---|
| 5,633,951 A * | 5/1997 | Moshfeghi | ................... | 382/154 |
| 6,633,657 B1 * | 10/2003 | Kump et al. | ................. | 382/128 |
| 2002/0141626 A1 * | 10/2002 | Caspi | ........................... | 382/131 |
| 2004/0249270 A1 * | 12/2004 | Kondo et al. | ................ | 600/425 |

FOREIGN PATENT DOCUMENTS

| | | |
|---|---|---|
| JP | 61-031125 | 2/1986 |
| JP | 03-236830 | 10/1991 |
| JP | 05-064638 | 3/1993 |
| JP | 07-051268 | 2/1995 |
| JP | 09-024034 | 1/1997 |
| JP | 09-094243 | 4/1997 |
| JP | 09-192131 | 7/1997 |
| JP | 10-151131 | 6/1998 |
| JP | 2002-207992 | 7/2002 |
| JP | 2003-099021 | 4/2003 |
| JP | 2004-165427 | 6/2004 |
| JP | 2004-222713 | 8/2004 |

* cited by examiner

Fig. 7
(a)
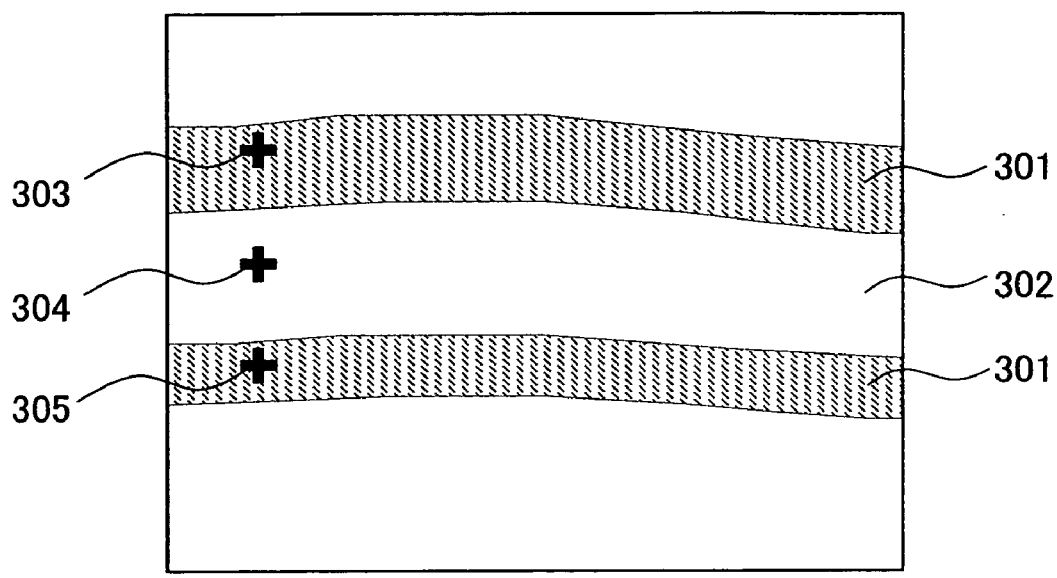
(b)
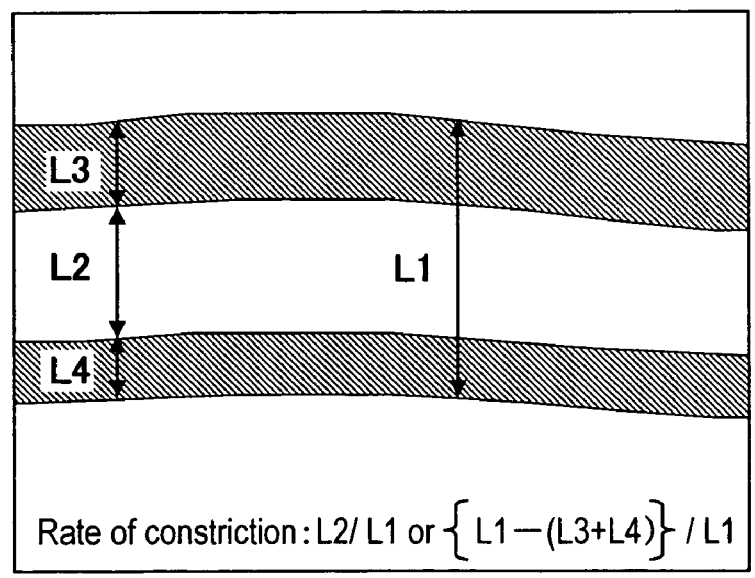
Rate of constriction: L2/ L1 or {L1−(L3+L4)} / L1

IMAGE DIAGNOSING SUPPORT METHOD AND IMAGE DIAGNOSING SUPPORT APPARATUS

TECHNICAL FIELD

The present invention relates to an image diagnosing support method and an image diagnosing support apparatus, and more particularly to a technique by which the region of an organ or the like is appropriately extracted from a plurality of images in the same region of an object displayed on the basis of a plurality of kinds of image data. This is an application involving a claim for Paris priority based on patent applications pertaining to Japanese Patent Application No. 2004-165427 and Japanese Patent Application No. 2004-222713 under the Japanese Patent Law.

BACKGROUND ART

An image diagnosing support system is proposed which acquires images of a region of one object to be examined by a plurality of medical imaging apparatuses to display the images. An object of such a system is to improve diagnostic skills, in particular to supplement observation of a region, which cannot be observed with one type of medical imaging apparatus, with other medical imaging apparatuses.

For instance, Patent Document 1 discloses an ultrasonic imaging apparatus which is provided with an image data input device enabling a plurality of images, including volume images from outside, to be inputted, and further provided with image position-associative display means which, when displaying a B mode image of a specific diagnosable region of a specific object to be examined, obtains a tomogram of the diagnosable region of the object in a position matching the tomographic position of the B mode image according to images from the image data input device, and positions the tomogram alongside or over the B mode image, or alternately displays them at regular intervals of time.

Patent Document 1: JP10-151131A

DISCLOSURE OF THE INVENTION

Problems to be Solved by the Invention

However, the ultrasonic imaging apparatus described in Patent Document 1 is nothing more than to automatically perform positional association (especially alignment) between a currently obtained B mode image and an analytical image of a similar region to it, obtained by an X-ray CT apparatus or an MRI apparatus, to make positional confirmation or the like of the desired region simply, rapidly and accurately, but it has no other function.

An object of the present invention is to provide an image diagnosing support method and an image diagnosing support apparatus by which the region of an organ or the like can be appropriately extracted when displaying an image in the same region of an object to be examined obtained by using a medical imaging apparatus. A further object of the present invention is to figure out the region of a blood vessel by using a region extracting method and measure the rate of constriction.

Means for Solving the Problems

In order to achieve the objects stated above, an image diagnosing support method according to the present invention comprises an acquisition step of acquiring a plurality of images obtained by imaging the same region of the same object with one or more medical imaging apparatuses and having positional information at the time when each of the images was picked up; a selecting step of selecting a first image and a second image out of the plurality of images; a displaying step of displaying the first image and the second image; a step of designating one or more of first reference points on the first image; a step of figuring out second reference points, on the second image, each matching one or another of the first reference points; a first step of extracting for each of the first reference points a first region containing that point within it; and a second step of extracting for each of the second reference points a second region containing that point within it, wherein either one of the first step and the second step is performed earlier or both are at the same time.

Moreover, an image diagnosing support method according to the present invention comprises a step of acquiring an image obtained by imaging a blood vessel of an object with a medical imaging apparatus, the image containing a blood vessel sectional region comprising a luminal region in which blood flows and a vascular tissue region; a step of extracting the luminal region and the vascular tissue region; a step of extracting from the luminal region and the vascular tissue region a plurality of parameters necessary for figuring out the rate of constriction of the blood vessel; and a step of calculating the rate of constriction of the blood vessel by using the plurality of parameters.

An image diagnosing support apparatus according to the present invention comprises: means for acquiring a plurality of images obtained by imaging the same region of the same object with one or more medical imaging apparatuses and having positional information at the time when each of the images was picked up; means for selecting two or more images out of the plurality of images; means for displaying the selected two or more images; means for designating one or more of first reference points on one of the selected two or more images; means for figuring out second reference points, on one or more images out of the selected two or more images, each matching one or another of the first reference points; and means for extracting for each of the first reference points a first region containing that point within it, and for each of the second reference points a second region containing that point within it.

Also, an image diagnosing support apparatus according to the present invention is provided with means for acquiring an image obtained by imaging an object with a medical imaging apparatus; and region extracting means for extracting a desired region out of the image, wherein the image contains a luminal region and a vascular tissue region of a desired blood vessel, the region extracting means extracts the luminal region and the vascular tissue region; and has means for figuring out from the luminal region and the vascular tissue region a plurality of parameters necessary for figuring out the rate of constriction of the blood vessel and means for calculating the rate of constriction of the blood vessel by using the plurality of parameters.

Advantages of the Invention

According to the present invention, it is possible to provide an image diagnosing support method and an image diagnosing support apparatus by which particularly the region of an organ or the like can be appropriately extracted when displaying an image in the same region of an object to be examined obtained by using a medical imaging apparatus. Further according to the present invention, the rate of constriction of a blood vessel can be accurately measured.

BRIEF DESCRIPTION OF THE DRAWINGS

FIG. 2(a) shows the result of region extraction in a medical image 10, out of two medical images 10 and 11, on the basis of a reference point 12, the reference point 12 being set in the medical image 10; FIG. 2(b) shows the result of setting in the medical image 11 a reference point 12a matching the reference point 12; FIG. 2(c) shows the result of region extraction in the medical image 11 on the basis of the reference point 12a; and FIG. 2(d) shows a state in which the boundary of an extraction region γ of the medical image 11 is displayed superposed over the medical image 10 and an extraction region β of the medical image 10 over the medical image 11;

FIG. 3(a) shows the result of region extraction in the medical image 10 on the basis of reference points 15 and 16, the reference points 15 and 16 being set in a short-axis line of a blood vessel; FIG. 3(b) shows the result of setting in the medical image 11 reference points 15a and 16a matching the reference points 15 and 16; FIG. 3(c) shows the result of region extraction in the medical image 11 on the basis of the reference points 15a and 16a; and FIG. 3(d) shows a state in which the extraction boundary of the medical image 11 is displayed superposed over the medical image 10;

FIG. 7(a) shows a case of setting reference points in the vascular tissue region and the luminal region; and FIG. 7(b) shows a case of computing the rate of constriction by measuring the diameters of the vascular tissue region and the luminal region;

DESCRIPTION OF SYMBOLS

Figure 1:
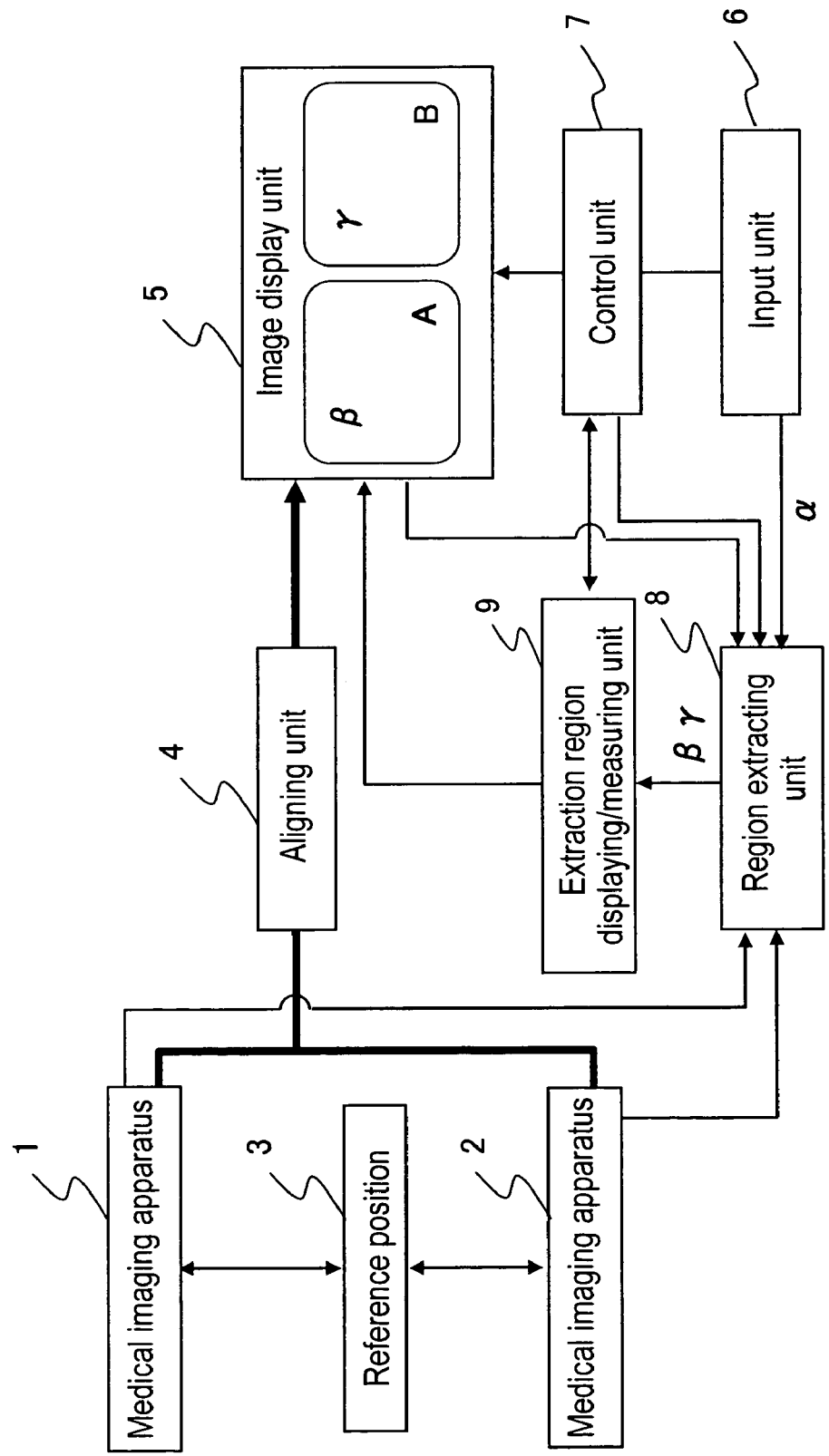
FIG. 1 shows the overall configuration of an image diagnosing support system pertaining to a first embodiment of the present invention.

1 Medical imaging apparatus
2 Medical imaging apparatus
3 Reference position
4 Aligning unit
5 Image display unit
6 Input unit
7 Control unit
8 Region extracting unit
9 Extracted region displaying/measuring unit
10 Medical image
11 Medical image
12 Reference point
12a Reference point
13 Display screen
14 Display screen
15 Reference point
15a Reference point
16 Reference point
16a Reference point
18 Medical image
19 Reference point
19a Reference point
20 Medical image
90 Medical image
91 Medical image
92 Display region
93 Hetero-angle image
94 Time-series image
95 Thumbnail image
96 Thumbnail image
97 Thumbnail image
100 Probe
102 Transceiver unit
104 Phasing unit
106 Blood flow rate computing unit
108 B image composing unit
110 DSC
112 Display unit
114 Control desk
116 Control unit
118 Region extraction calculating unit
119 Blood flow signal determining unit
120 Image data extracting unit
121 Constriction rate calculating unit
200 Focus
201 Region
202 Region
203 Reference point
204 Reference point
205 Approximate circle
206 Approximate circle
301 Region
302 Region
303 Reference point
304 Reference point
305 Reference point
1300 Display screen
1301 Display screen
1302 Display screen

MODES FOR CARRYING OUT THE INVENTION

Preferred embodiments of the present invention will be described below with reference to drawings.

<First Embodiment>

A first embodiment is an embodiment in which matching regions are extracted two or more medical images.

FIG. 1 shows the overall configuration of an embodiment of an image diagnosing support system to which the present invention is applied. Here is considered a case in which medical images are simultaneously formed by two different kinds of medical imaging apparatuses. In the following description, the two medical images displayed on the screen will be denoted as a medical image A and a medical image B for the sake of convenience.

According to FIG. 1, the image diagnosing support system comprises a medical imaging apparatus 1, a medical imaging apparatus 2, a reference position 3 which determines a spatial reference needed for the relative alignment of the medical images acquired by the medical imaging apparatuses 1 and 2, an aligning unit 4 which aligns the medical images acquired by the medical imaging apparatuses 1 and 2, an image display unit 5 which simultaneously displays the medical images, an input unit 6 which selects or instructs a region of extraction regions, a region extracting unit 8 which performs region extraction, an extraction region displaying/measuring unit 9 which displays the region obtained by the region extracting unit 8 on the image display unit 5 in various forms and measures the long/short axial lengths of the extraction region, and a control unit 7 which controls the display selection of the two different medical image A and medical image B, the selection of the region of the extraction regions, the selection of the region extracting method, the selection of the measuring items of the extraction regions, and the like. In this embodiment, the medical imaging apparatus 1 is comprised of an ultrasonic imaging apparatus which is a medical imaging apparatus capable of displaying a medical image on a real-time basis. The medical imaging apparatus 2 is comprised of an X-ray CT apparatus or an MRI apparatus, which is a medical imaging apparatus by which the region contour of the medical image can be picked up in a clearly readable way. The X-ray CT apparatus or the MRI apparatus generates image data by imaging the same region of the same object at a different time from the time at which the ultrasonic imaging apparatus picks up a medical image. Therefore in this embodiment, two different images picked up from the same region of the same object are displayed by the image display unit 5 on the basis of image data picked up by the ultrasonic imaging apparatus on a real-time basis and image data picked up by the X-ray CT apparatus or the MRI apparatus in the past (namely at a different time from the time at which the ultrasonic imaging apparatus picked up its image). Incidentally, the combination of image data is not limited to the above-stated. For instance, the medical imaging apparatus 1 may be comprised of an ultrasonic imaging apparatus and the medical imaging apparatus 2, which is an X-ray CT apparatus or an MRI apparatus, both generating image data on a real-time basis, and the image display unit 5 may display two real-time images. Or the medical imaging apparatus 1 may be comprised of an ultrasonic imaging apparatus and the medical imaging apparatus 2, which is an X-ray CT apparatus or an MRI apparatus, and they may pick up images at different times in the past to generate image data. And the image display unit 5 may display images on the basis of the two sets of image data picked up at the different times in the past. Further, the medical imaging apparatus 1 need not be an ultrasonic imaging apparatus, but the medical imaging apparatus 1 may be an X-ray CT apparatus, and the medical imaging apparatus 2, an MRI apparatus.

Next, the flow of processing by the image diagnosing support system of FIG. 1 will be described.

First, the medical imaging apparatuses 1 and 2 respectively pick up a medical image A and a medical image B. For instance, the medical imaging apparatus 1 is an ultrasonic imaging apparatus, and the medical imaging apparatus 2 is an MRI (magnetic resonance imaging) apparatus. Each has its own position identifying means, and the spatial position of the data obtained by the medical imaging apparatuses 1 and 2 is identified with reference to a reference position 3 common to them (as the origin). For instance, where the medical imaging apparatus 1 is an ultrasonic imaging apparatus, the spatial position of the image having the reference position as its origin is identified by using a magnetic sensor or the like. This enables the spatial positional relationship to the same position as what was obtained by the MRI of the medical imaging apparatus 2 to be identified. The medical image data obtained by the respective medical imaging apparatuses are identified as spatial coordinates by the aligning unit 4 and displayed on the image display unit 5. This procedure enables the same region in the medical images obtained by the two different medical imaging apparatuses to be simultaneously displayed on the same screen. The aligning means may as well be comprised as means which, as described in Patent Document 1 for instance, displays an ultrasonic tomographic plane being examined by an ultrasonic imaging apparatus and the tomogram of an X-ray CT apparatus or the tomogram of an MRI apparatus corresponding to it on the same screen as the ultrasonic tomogram by detecting the relative position of the object to a probe and its direction in an arbitrarily set coordinate space and performing calibration in a three-dimensional coordinate space to make possible alignment between the image data from the image data input device and different regions of the object and thereby detecting positional relationships between tissues in the diagnostic image and the body surface (the position of the probe).

How this takes place will be described with reference to FIG. 2.

First, the image diagnosing support system reads in the medical image data obtained by the medical imaging apparatus 1 and the medical image data obtained by the medical imaging apparatus 2. And the image display unit 5 displays medical images based on these medical image data.

The user selects, out of these medical images, an image for region extraction. In this embodiment, the user selects a medical image 10.

The user sets a reference point 12 in the medical image 10 by using the input unit 6. The reference point 12 is one point contained in an extraction region desired by the user (the reference point 12) in the medical image 10. The user further inputs extraction conditions α.

The region extracting unit 8 extracts the desired region containing the reference point 12 (hereinafter referred to as the "extraction region β") in accordance with the inputted extraction conditions α. FIG. 2(a) shows a state in which the user-desired region has been extracted by the region extracting unit 8.

Available methods of region extraction include one of region extraction based on brightness information on the image and another of region extraction based on waveform data. In the case of the former, brightness information on the image earlier selected by the input unit is delivered from the image display unit 5 to the region extracting unit 8.

The region extracting unit 8 performs extraction on the basis of the brightness information on the received image. The region extracting unit 8 extracts an extraction region β by successively comparing pixel values near the reference point 12 set in the medical image 10 with the predetermined threshold value (region growing). The region extracting unit 8 may use some known techniques other than region growing, such as the snake method.

In the latter case, on the other hand, signals received from the object are delivered from medical imaging apparatuses to the region extracting unit 8 directly. The region extracting unit 8 performs region extraction by using the received signals received from the object.

Next, the obtained region data β are delivered to the extraction region displaying/measuring unit 9. The user inputs screen display conditions by using the input unit 6 and determines them. The screen display unit 5 displays the extraction region β in the image earlier selected by the input unit 6 (the medical image 10 in this embodiment). The screen display conditions are conditions regarding the displaying, such as displaying the whole with the extraction region colored or displaying only the contour, for instance. It is also possible here to measure the extraction region, and measure such items of geometric information as the region, long axis and short axis, long diameter and short diameter, or characteristic quantities of the extraction region.

At the same time, region extraction of the same region as the reference point 12 selected by the medical image 10 is automatically performed in the medical image 11. More specifically, positional information positional coordinates on the extraction reference point 12 selected by the medical image 10 is delivered to the medical image 11.

Figure 2:
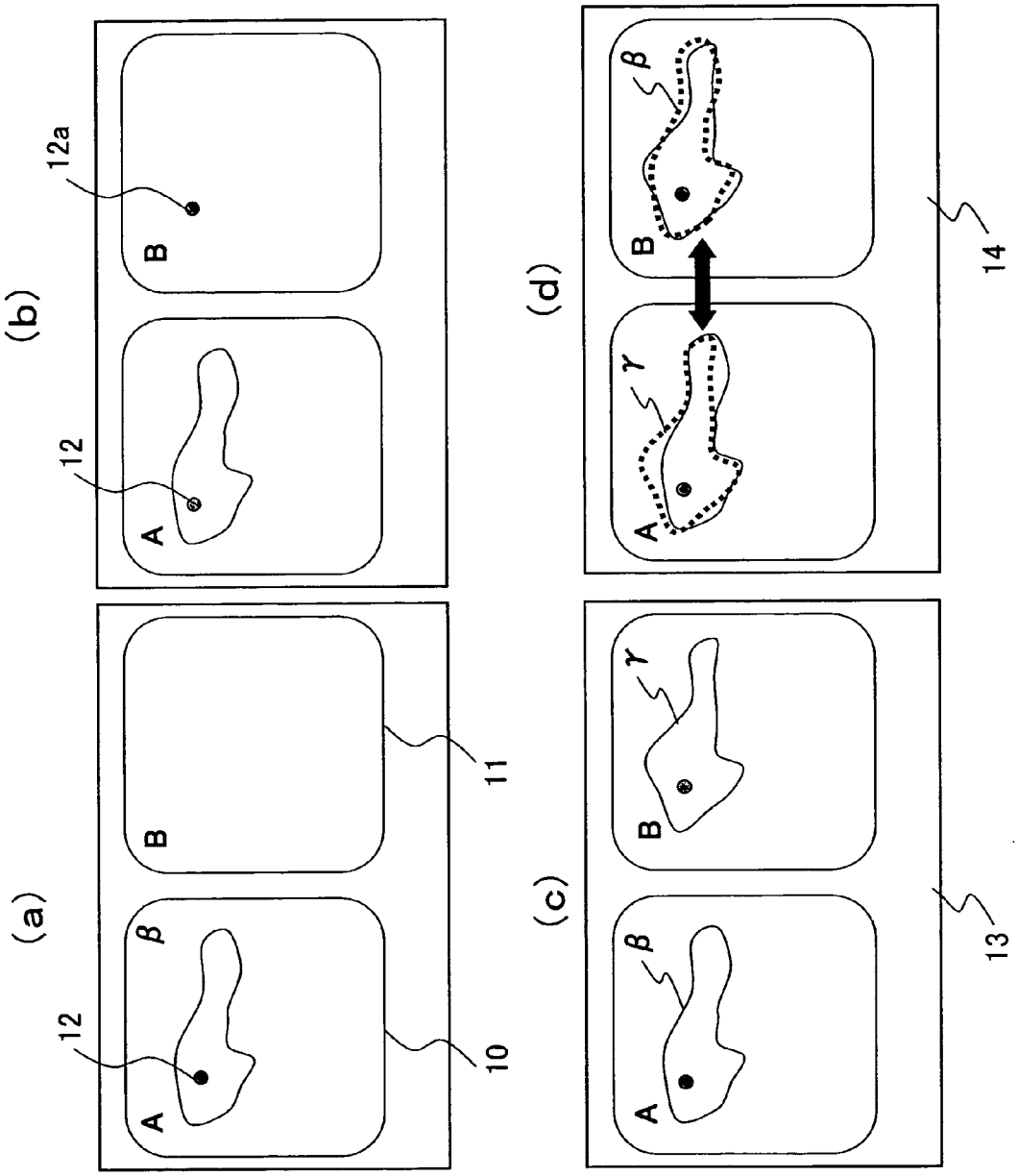

FIG. 2(*b*) shows the result of setting a point matching the reference point 12 in the medical image 11 (hereinafter referred to as the "reference point 12*a*") by the extraction region displaying/measuring unit 9 on the basis of the delivered positional information on the reference point 12.

Next, the region extracting unit 8 executes region extraction on the basis of the reference point 12*a*. The method of region extraction that is executed is determined by the user selection by using the input unit 6. As the method of region extraction, what seems to be the most suitable for each medical image can be selected. The method of region extraction and the extraction conditions that are executed on the medical image 11 may be either the same as or different from those used for the medical image 10.

FIG. 2(*c*) shows the result of region extraction executed by the region extracting unit 8 on the basis of the reference point 12*a* to extract the extraction region γ. The extraction region β extracted from the medical image 10 and the extraction region γ extracted from the medical image 11 are displayed on a display screen 13.

The extraction region γ obtained as the result of extraction is delivered to the extraction region displaying/measuring unit 9 as in the previous case. And after determining the screen display conditions, the extraction region displaying/measuring unit 9 generates data for display in which the boundary of the extraction region γ is superposed over the extraction region β of the medical image 10 and data for display in which the boundary of the extraction region P is superposed over the extraction region γ of the medical image 11, and transmits them to the image display unit 5. The image display unit 5 displays these data for display.

FIG. 2(*d*) shows a state in which the boundary of a region extracted from one medical image is displayed superposed over the other extraction region. An image in which the boundary of the extraction region γ is superposed over the extraction region β, and an image in which the boundary of the extraction region β is superposed over the extraction region γ are displayed on a display screen 14.

By the operation described above, a plurality of medical images containing the same sectional image obtained by imaging the same region of the same object with different medical imaging apparatuses can be displayed on the same screen. Furthermore, by performing region extraction of any desired region in any desired one medical image out of the aforementioned two medical images, region extraction of the same region can be automatically performed in the other medical image.

The present invention is not limited to the above-described embodiment, but can be implemented in various modified embodiments without deviating from the essentials of the invention.

For instance, though the foregoing embodiment was described with reference to a plurality of medical images picked up with different medical imaging apparatuses, similar processing to the embodiment described above may be performed on the basis of a plurality of medical images picked up with the same medical imaging apparatus (for instance, sectional images of the same region of the same object picked by using the same MRI apparatus at different times).

Further, though the foregoing embodiment was described with reference to a plurality of medical images picked up with different medical imaging apparatuses, medical images picked up with different medical imaging apparatuses of the same type can as well be used. For instance, medical images taken of the same region of the same object with a plurality of ultrasonic diagnostic apparatuses may also be used.

In the foregoing embodiment, first the reference point 12 is set, and the extraction region β is extracted on the basis of the reference point 12. And the reference point 12*a* is set, and the extraction region γ is extracted on the basis of the reference point 12*a*. However, the reference points 12 and 12*a* are set according to the medical images 10 and 11; region extraction in the medical image 10 and region extraction in the medical image 11 may be accomplished simultaneously, or the extraction region γ is first extracted from the medical image 11, followed by extraction of the extraction region β from the medical image 10.

Further in the foregoing embodiment, there are supposed to be two medical imaging apparatuses, but there may be three or more medical images.

For instance, three medical imaging apparatuses display the same region simultaneously on the same screen, and generate three different sets of medical image data. The image diagnosing support system reads in these sets of medical image data, and displays medical images on the image display unit 5 on the basis of these medical image data. The user selects three medical images (one for each medical imaging apparatus) for processing region extraction out of the displayed medical images. The image diagnosing support system displays, for each of the three medical images, the boundaries of regions extracted from the two other medical images superposed one over the other.

More specifically, for the first medical image, a region extracted from the first medical image is displayed by using a solid line and color discrimination. The contour line (boundary) of an extraction region extracted from a second medical image is displayed in a one-dot chain line superposed over that region extracted from the first medical image. Further, the contour line of an extraction region extracted from a third medical image is displayed superposed in a dotted line.

For the second medical image, a region extracted from the second medical image is displayed by using a thin solid line and color discrimination. The contour line of an extraction region extracted from the first medical image is displayed superposed over a region extracted from the second medical image. Further, the contour line of an extraction region extracted from the third medical image is displayed superposed in a dotted line.

Further, for the third medical image, a region extracted from the third medical image is displayed by using a thin solid line and color discrimination. The contour line of an extraction region extracted from the first medical image is displayed in a thick solid line superposed over a region extracted from the third medical image. Further, the contour line of an extraction region extracted from the second medical image is displayed superposed in a one-dot chain line.

The number of sets of data to be superposed over the extraction region extracted from the first medical image may be three or two, selectable by the user as desired. It is also selectable as desired the result of region extraction from which image is to be superposed over which image.

Whereas a medical imaging apparatus which, regarding two or more medical imaging apparatuses, simultaneously displays the same region on the same screen and extracts the same region has been described so far, the medical imaging apparatuses 1 and 2 shown in FIG. 1 need not be actually fitted as they are. For instance as disclosed in Patent Document 1, a plurality of images, including volume images from outside, may be inputted to be used as input data and similar processing done.

While a case in which images obtained by using the medical imaging apparatuses are shown in different parts (left and right) of the same screen was shown regarding this embodiment, a plurality of images may as well be shown in the same part of the screen superposed one over the other. For instance, the extraction region γ may be shown superposed over the extraction region β of the medical image 10.

Further, the region of region extraction from images obtained by different medical imaging apparatuses need not be the same, but there may be different regions. For instance, if an image obtained by an ultrasonic imaging apparatus is subjected to region extraction of the heart, and an image obtained by an MRI apparatus, to region extraction of a lung for superposed displaying, there will be no deviation from the essentials of the invention. In this embodiment, region information on regions which would not be clear enough with only one medical imaging apparatus can be obtained more accurately, and will become available for application to and assistance in various treatments and diagnoses.

<Second Embodiment>

Figure 3:
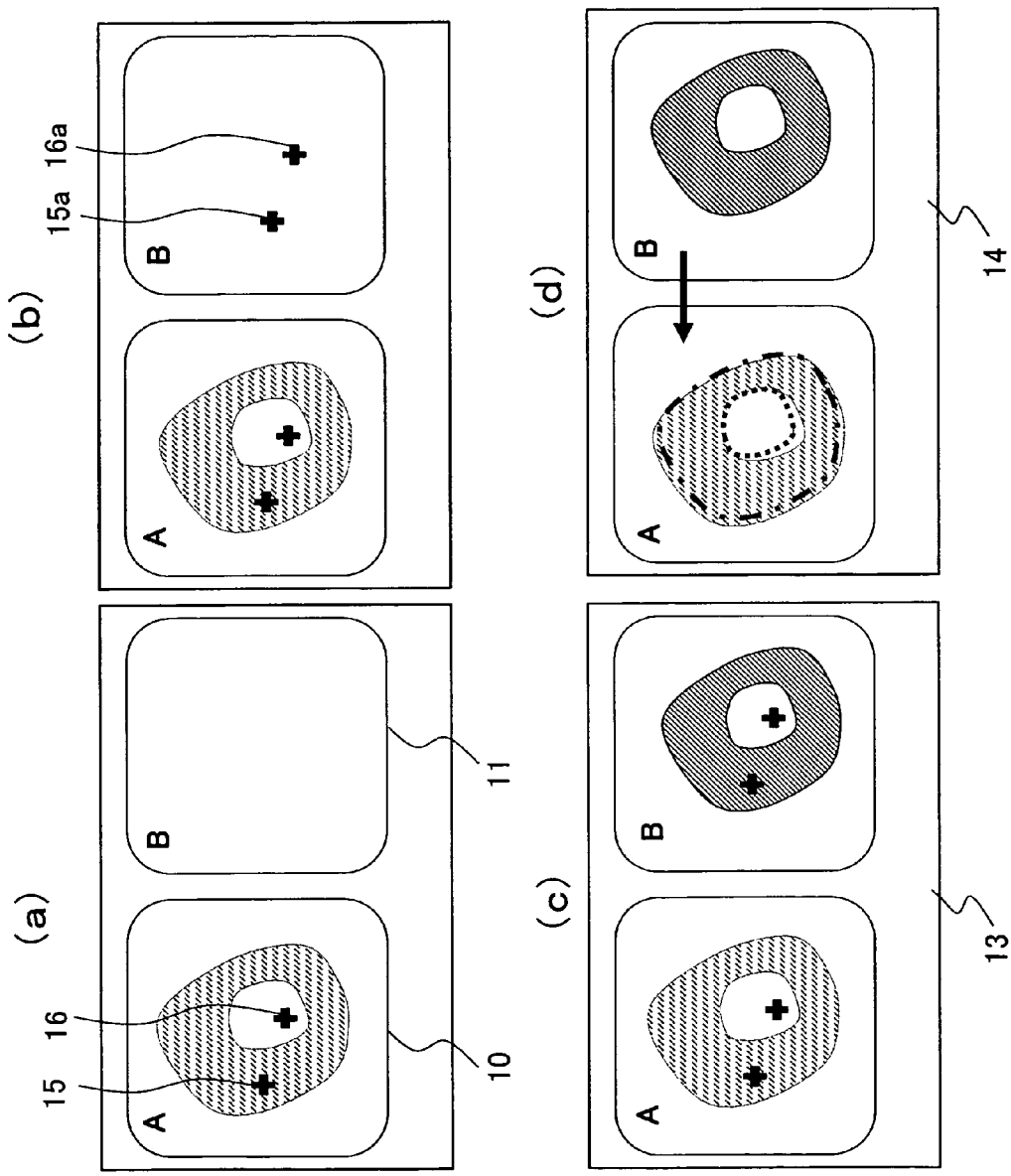

The second embodiment is an embodiment in which the rates of constriction of blood vessels are figured by using the region extraction method in the first embodiment. While the number of reference points first designated by the user is one in the first embodiment, this embodiment is different in that the user designates two reference points, but it is similar to the first embodiment in other respects. The second embodiment will be described below with reference to FIGS. 3. FIGS. 3 are diagrams illustrating the processing to extract a region wherein the rate of constriction of a blood vessel is to be figured out from the medical image 10.

The user sets in the medical image 10 containing the short-axis line of the blood vessel reference points 15 and 16 respectively in a vascular tissue region constituting the blood vessel region (hereinafter referred to as the "tissue region") and a luminal region (the region in which blood flows). The region extracting unit 8 extracts the tissue region and the luminal region from the medical image 10 on the basis of those reference points 15 and 16. FIG. 3(a) shows the result of this extraction.

Next, reference points 15a and 16a matching the reference points 15 and 16 are set in the medical image 11. FIG. 3(b) shows the result of the setting of the reference points 15a and 16a.

The region extracting unit 8 extracts regions on the basis of the reference points 15a and 16a. FIG. 3(c) shows the result of this extraction.

The extraction region displaying/measuring unit 9 generates data for display in which the boundary of the extraction region of the medical image 11 is superposed over the extraction region of the medical image 10, and transmits them to the image display unit 5. The image display unit 5 displays these data for display. FIG. 3(d) shows a state in which the boundary of the extraction region of the medical image 11 is superposed over the medical image 10.

In the embodiment described above the tissue region and the luminal region of a blood vessel are extracted. On the basis of these tissue region and luminal region, the rate of constriction of the blood vessel is figured out. The method of calculating the rate of constriction of the blood vessel will be described afterwards with reference to FIG. 6.

<Third Embodiment>

Figure 4:
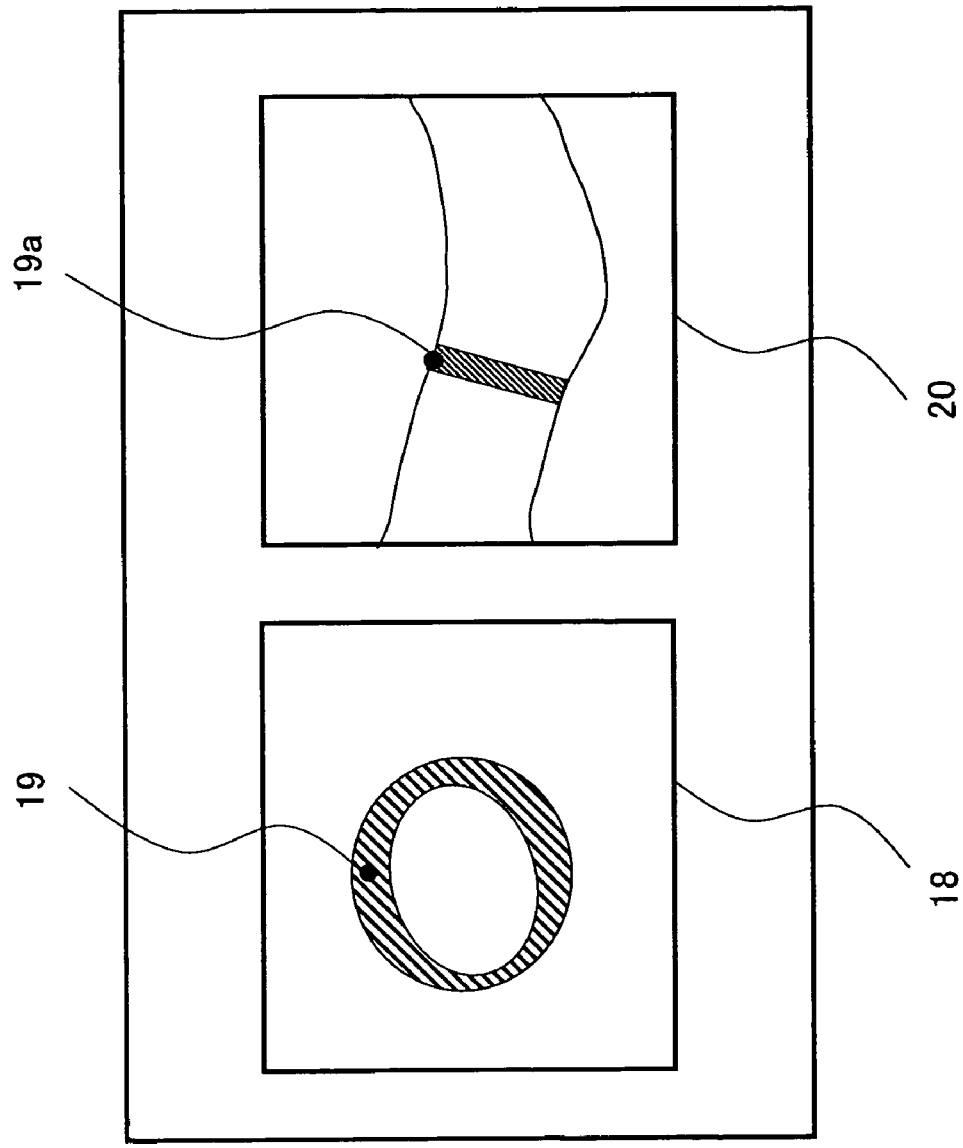
FIG. 4 shows how two images are displayed by a single medical imaging apparatus and a process of region extraction.

In the third embodiment, sets of image data obtained by imaging the same region of the same object with a single medical imaging apparatus from different angles are displayed side by side, and an extraction region extracted from one medical image is automatically extracted into the other medical image. FIG. 4 shows an example of screen display in this embodiment.

A medical image 18 in FIG. 4 is a medical image picked up of a section of a blood vessel of the same object. A medical image 20 in FIG. 4 is a medical image picked up sideways of the blood vessel having this blood vessel section. When the user designates with the input unit 6 one point 19 in the vascular tissue region of the medical image 18, a vascular tissue region with reference to 19 is extracted. This extracted vascular tissue region is represented by the hatched part in the medical image 18. The region extracting unit 8 extracts a point 19a matching 19 in the medical image 20. And it performs region extraction from the medical image 20 a region containing the point 19a and matching the vascular tissue region containing 19 in the medical image 18. Incidentally, the region matching the vascular tissue region containing the point 19a should essentially correspond to a linear (one-pixel) region in the medical image 20, it may as well be displayed as a strip-shaped region containing the point 19a and having a width of a few pixels from left to right. This enables the visibility to be better than in linear displaying.

<Fourth Embodiment>

Regarding the fourth embodiment, the description will focus on an ultrasonic imaging apparatus as a specific example of medical imaging apparatus.

Figure 5:
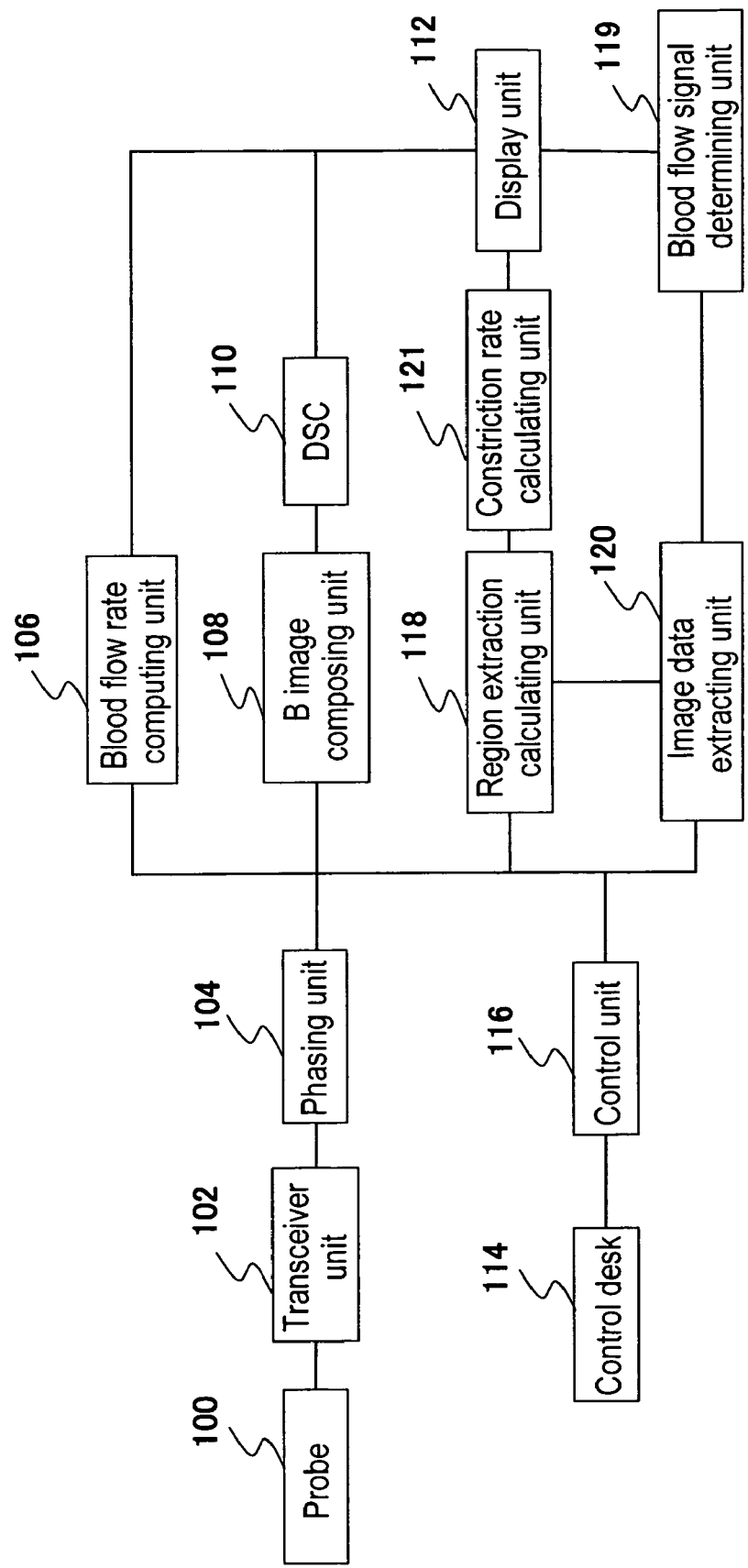
FIG. 5 shows the overall configuration of an ultrasonic imaging apparatus pertaining to a fourth embodiment of the present invention.

The ultrasonic imaging apparatus, as shown in FIG. 5, is provided with a probe 100 which transmits an ultrasonic wave to an object to be examined (not shown) and receives a reflected echo signal from the object, a transceiver unit 102 which generates a signal for driving the probe 100 and subjects the reflected echo signal to signal processing such as amplification, a phasing unit 104 which phases the reflected echo signal having undergone signal processing, a blood flow rate computing unit 106 which computes the blood flow rate, a B image composing unit 108 for displaying the phased signal as a B image, a digital scan converter unit (DSC) 110 which performs scan conversion into monitor scanning lines, a display unit 112 which displays the signal having undergone the scan conversion, an image data extracting unit 120 which sets a region of interest (ROI) in the image displayed on the display unit 112, a region extraction calculating unit 118 which extracts a region in the set ROI, a constriction rate calculating unit 121 which calculates the rate of constriction from the region figured out by the region extraction calculating unit 118, a control unit 116 which controls the transceiver unit 102, the phasing unit 104, the blood flow rate computing unit 106, the region extraction calculating unit 118 and the image data extracting unit 120, and a control desk 114 from which the operator inputs various control information to the control unit 116.

The blood flow rate computing unit 106, which is to input the reflected echo signal obtained by the transceiver unit 102 and to take out a frequency signal having undergone a Doppler shift by the blood in the object, has a local oscillator which generates a reference frequency signal oscillating the vicinities of the frequency of the ultrasonic wave transmitted and received by the probe 100; a 90-degree phase shifter which shifts the phase of the reference frequency signal from this local oscillator by 90 degrees for instance; a mixer circuit which multiplies the reflected echo signal by the reference frequency signal from the local oscillator or the 90-degree phase shifter; and a high frequency filter which takes out the low frequency component from the output of this mixer circuit.

The blood flow rate computing unit 106, which computes the blood flow rate in the object by using a frequency signal having undergone a Doppler shift outputted from a Doppler demodulator circuit (hereinafter referred to as the "Doppler signal"), has within it an average velocity computing section which figures out from the Doppler signal inputted to it the average velocity of the blood flow in the blood vessel in the diagnosed region and a velocity variance computing section which figures out the velocity variance of the blood flow. Data obtained via the blood flow rate computing unit 106 are inputted and converted into color signals according to the state of the blood flow, and digital signals are converted into video signals.

The display unit 112 displaying the color signals (video signals) which are outputted and inputted to it, distinguished in color, red and blue for instance, is comprised of a TV monitor capable of color displaying.

The blood flow signal determining unit 119 determines the presence or absence of any blood flow signal by measuring whether or not there are color signals (whether or not there are Doppler signals) in the image resulting from the visualization by the display unit 112 of the Doppler signals figured out by the blood flow rate computing unit 106.

The image data extracting unit 120 sets regions of interest (ROI) in the displayed image. The size and direction (angle) of these regions of interest can be altered by the operator as desired. Instead of setting rectangular or oval regions of interest, arrangement may be so made in advance as to display only a region surrounded by a thick solid line on the display unit 112, and the region surrounded by the thick solid line treated as the region of interest. This region of interest, intended for detecting the blood flow rate in the diagnosed region of the object, is set on the B image in a position where there is the carotid blood vessel, for instance.

Figure 6:
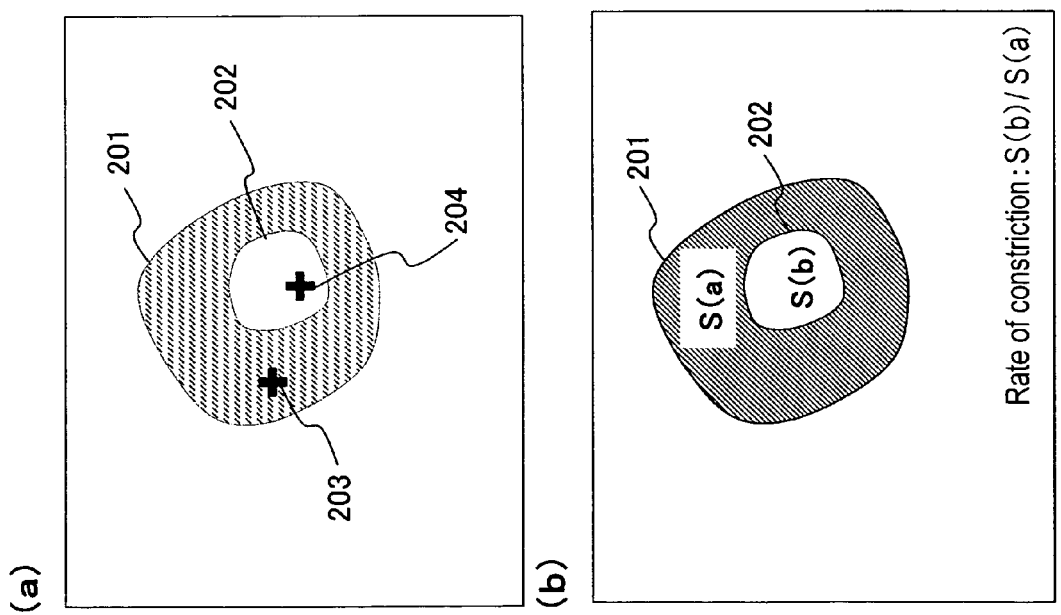
FIG. 6(a) shows a case of setting reference points in a vascular tissue region and a luminal region.
FIG. 6(b) shows a case of computing the rate of constriction by measuring the regions of the vascular tissue region and the luminal region.
FIG. 6(c) shows a case of computing the rate of constriction by measuring the diameters of the vascular tissue region and the luminal region.

Next, the region extraction calculating unit 118 will be described with reference to FIGS. 6. The region extraction calculating unit 118 sets as a reference point 204 one point in a region, within the region of interest set by the image data extracting unit 120, where the blood flow signal determining unit 119 has determined the presence of a blood flow signal. And it sets a threshold, or a threshold range, for having the range of pixel values in the region recognized. For instance, using a threshold range "47" where the pixel value "3" of the reference point displayed on the display unit 112, the threshold is given by "3±47". Namely, the lower threshold is "−4" and the upper threshold, "50". The control unit 116 searches pixels around the reference point 204, and links a region having pixel values within the range of thresholds. Eventually, a region 202 containing the reference point 204 and having pixel values within the range of thresholds is obtained. The region 202 is the luminal region of the blood vessel in which blood flows.

And a reference point 203 is set in the region outside the region 202. Setting of the reference point in a constricted region is present in advance to be, for instance, 1 mm outside the region 202. The control unit 116 searches pixels around the reference point 203, and links a region having pixel values within the range of thresholds. Eventually, a region 201 containing the reference point 203 and having pixel values within the range of thresholds is obtained. The region 201 is the vascular tissue region constituting the blood vessel wall.

FIG. 6(a) shows the region 202, the region 201 positioned around it, and the reference points 204 and 203 contained in the region 202 and the region 201.

Next, square measures S(a) and S(b) of the region 201 and the region 202 are figured out as shown in FIG. 6(b). For the square measures of these regions, the square measures of the region of pixels, namely the numbers of pixels, are calculated by the region extraction calculating unit 118. And the rate of constriction is figured out according to Equation 1 by the constriction rate calculating unit 121.

[Equation 1]

$$\text{Rate of constriction} = S(b)/S(a) \tag{1}$$

And the rate of constriction so figured out is displayed on the display unit 112. Incidentally, since the rate of constriction is a relative value, the diameters of approximate circles 205 and 206 may be figured out instead. For instance, as shown in FIG. 6(c), the rate of constriction may be calculated according to Equation 2 by figuring out the square measures S(a) and S(b) and approximating the square measures so figured out to circles as circular constant×radius×radius to figure out the diameter (radius×2) of the circle. Or, L1 and L2 may as well be figured out by directly measuring the respective long axes of the region 201 and the region 202.

[Equation 2]

$$\text{Rate of constriction} = L2/L1 \tag{2}$$

And the rate of constriction figured out is displayed on the display unit 112. Although the foregoing description referred to measurement of the rate of constriction by extracting a region in the short-axis direction of the carotid, the rate of constriction can also be measured in the long-axis direction.

A specific example of measurement of the rate of constriction by region extraction in the long-axis direction is shown in FIGS. 7. The region extraction calculating unit 118 sets as a reference point 304 one point in a region, within the region of interest set by the image data extracting unit 120, where the blood flow signal determining unit 119 has determined the presence of a blood flow signal. It sets a threshold, or a threshold range, for having the range of pixel values in the region recognized.

The control unit 116 searches pixels around the reference point 304, links a region having pixel values within the range of thresholds, and a region 302 containing the reference point 304 and having pixel values within the range of thresholds is obtained. If the extent of the region 302 reaches the ends of the screen, the region 302 is linked to the ends of the screen. This region 302 is a luminal region.

And on both outsides of the region 302, a reference point 303 and a reference point 305 are set in two positions. For instance, the region extraction calculating unit 118 designates the reference point 303 and the reference point 305 as external points 0.5 mm away from the ends of the region 302. On the bases of these reference point 303 and reference point 305, in the same way as in FIG. 6, a region 301, which is a vascular tissue region, is extracted. FIG. 7(a) shows the regions 301 and 302 and the reference points 303, 304 and 305.

Next, the rate of constriction of the blood vessel is measured by using the region 301 and the region 302. As shown in FIG. 7(b), the diameter of the section is measured in the axial direction of the blood vessel. And the constriction rate calculating unit 121 figures out the rate of constriction according to Equation 3.

[Equation 3]

$$\text{Rate of constriction} = L2/L1, \text{rate of constriction} = \{(L1-(L3+L4))/L1\} \quad (3)$$

The display unit 112 displays this rate of constriction so figured out. In this way, it is possible to figure out the region of the blood vessel in the short-axis direction or the long-axis direction by using the region extraction method to measure the rate of constriction.

It is also possible for the constriction rate calculating unit 121 to calculate the average of the rate of constrictions measured in the long-axis direction and the short-axis direction by sliding the probe 100 in the section where the rate of constriction was figured out in the long-axis direction thereby to figure out the rate of constriction in that section in the axial direction, and to have the average displayed on the display unit 112. Therefore, it is possible to measure the rate of constriction with even higher accuracy.

Figure 8:
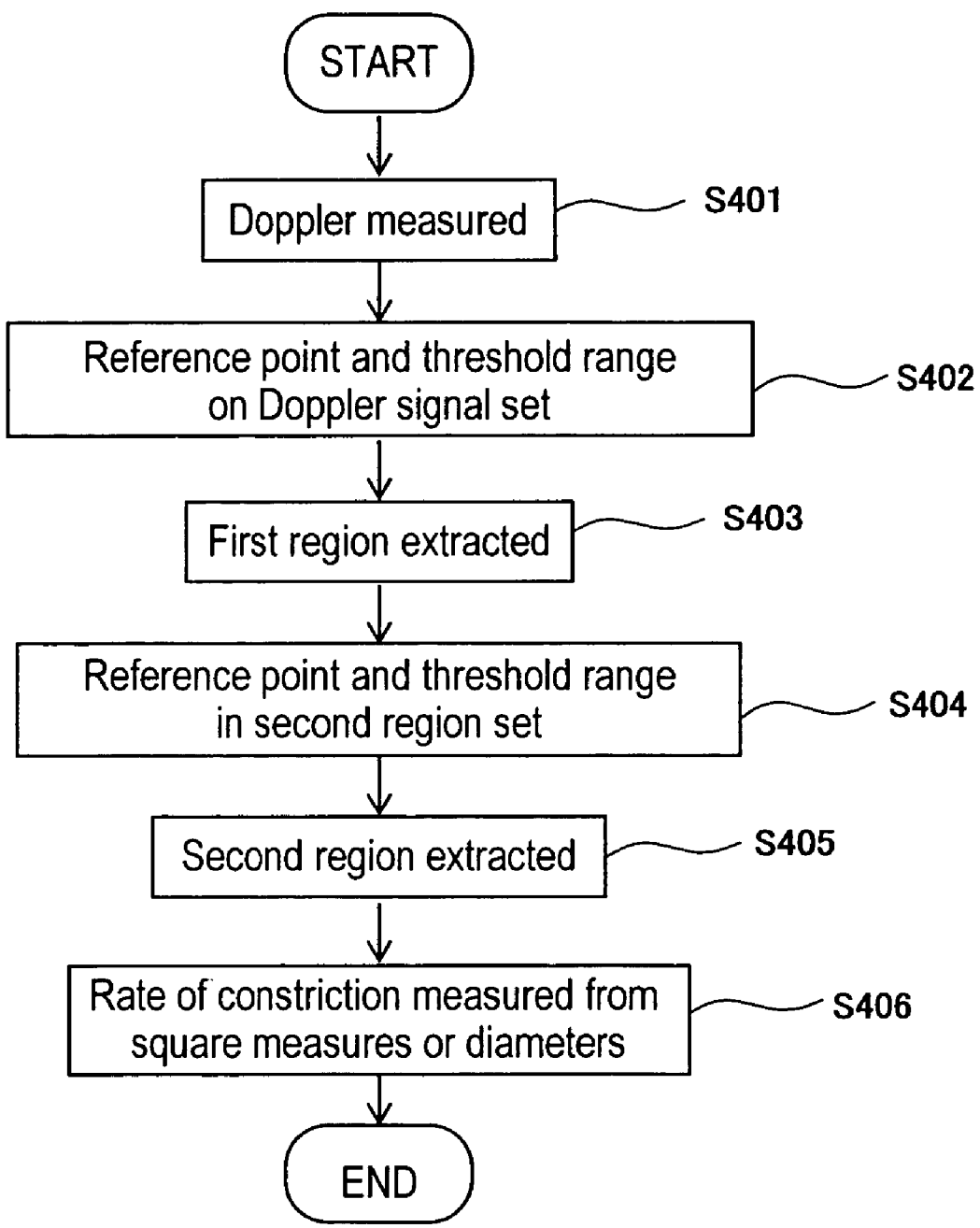
FIG. 8 is a flow chart shoring the flow of processing in the fourth embodiment.

Next, the operational procedure in this embodiment will be described with reference to FIG. 8. FIG. 8 is a flow chart showing the flow of processing in this embodiment.

At S401, the blood flow rate computing unit 106 measures a Doppler signal (step 401). At S402, the region extraction calculating unit 118 sets a reference point where there is the Doppler signal and further sets the threshold range of pixels (step 402).

At S403, the region extraction calculating unit 118 searches pixels around the reference point 204, links a region having pixel values within the range of thresholds, obtains the region 202 containing the reference point 204 and having pixel values within the range of thresholds, and extracts a first region (step 403).

At S404, the region extraction calculating unit 118 sets the reference point 203 in a region outside the first region, and further sets the threshold range of pixels (step 404).

At S405, the region extraction calculating unit 118 searches pixels around the reference point 203, links a region having pixel values within the range of thresholds, obtains the region 201 containing the reference point 203 and having pixel values within the range of thresholds, and extracts a second region (step 405).

At S406, the constriction rate calculating unit 121 calculates the rate of constriction by using the square measures or diameters of the first region and the second region (step 406).

Although reference points are supposed to be set by the region extraction calculating unit 118 according to the invention, they may as well be manually set by using the control desk 114. Further, though the foregoing description referred to an embodiment in which the invention is applied to an ultrasonic imaging apparatus, the invention may as well be applied to some other medical imaging apparatus which images an object to be examined and generates image data, such as an X-ray CT apparatus, an MR apparatus, X-ray imaging apparatus or the like instead of an ultrasonic imaging apparatus.

Although the foregoing description referred to means for figuring out the rate of constriction by which the square measures of the luminal region and of the vascular tissue region are calculated from independent reference points by respectively desired region extraction methods, the tubule region extraction may as well be directly figured out of the Doppler signal indicating the region in which a blood flow is present. The Doppler signal which indicates presence of the blood flow is usually displayed in color on a monitor. When the reference point 203 for extracting a vascular tissue region is prescribed and the vascular tissue region is found out by the above-described region extraction method for instance, the luminal region in which a blood flow is present is displayed on the monitor with color information inside the vascular tissue region. It is possible to extract the luminal region merely by counting the number of pixels having that color information.

Although a case in which the Doppler signal having information on blood presence or absence is used for luminal region extraction has been described, what gives information on blood presence or absence is not limited to the Doppler signal. Signals obtained by any diagnostic method permitting discriminative displaying of a blood flow or a region in which a blood flow is present and the peripheral tissues can be used.

Figure 12:
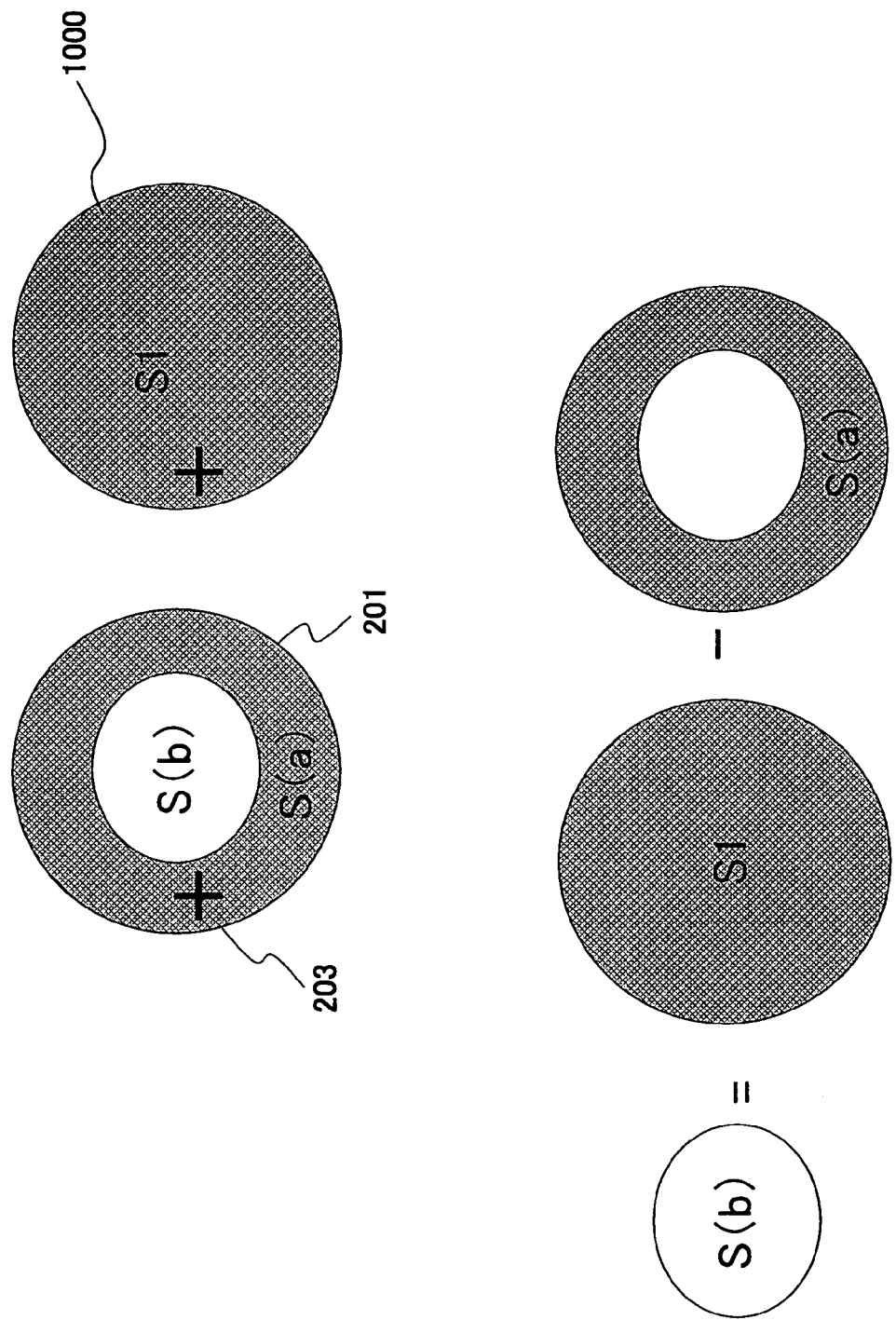
FIG. 12 shows a method of calculating a luminal region.

Further, the luminal region need not be directly found out by region extraction, but can also be extracted merely by finding out the vascular tissue region. A case of the short axis of a blood vessel for instance will be described. As shown in FIG. 12, the vascular tissue region 201 can be obtained by region extraction from the reference point 203 by using the above-described technique. The blood vessel region including the vascular tissue region and the luminal region is defined as the outermost inside 1000 of the vascular tissue region, and its square measure is given by S(1). The luminal region can be figured out by determining the balance of subtraction of a square measure S(a) from the outermost inside 1000 of the vascular tissue region 201. The rate of constriction can also be figured out by the method shown in FIGS. 6. By this method, independent reference points need not be obtained from both the vascular tissue region and the luminal region, but the rate of extraction can be figured out by indicating a reference point only in the vascular tissue region and performing region extraction.

[Equation 4]

$$\text{Luminal region square measure } S(b) = \text{Blood vessel region square measure } (S1) - \text{Vascular tissue region square measure } (S(a)) \quad (4)$$

This can be similarly accomplished regarding the long axis of the blood vessel, too.

Although derivation of the rate of constriction of the blood vessel has been described so far, the rate of constriction can be similarly achieved for any other region needing its derivation.

<Fifth Embodiment>

The fifth embodiment is one example of utilization of the result of region extraction after region extraction from two medical images.

An image diagnosing support system in this embodiment has means for executing automatic adjustment of the display parameters of image displaying to make the extraction region especially well perceptible (gain/dynamic range automatic adjusting function). The gain/dynamic range automatic adjusting function may be executed by the extraction region displaying/measuring unit 9 in the first embodiment or gain/ dynamic range automatic adjusting means may be provided in addition to the constituent elements in the first embodiment and the fourth embodiment.

The gain/dynamic range automatic adjusting function is a function to so adjust the gain/dynamic range as to match the distribution range of the image signal values in the extraction region with the maximum gradation range of image displaying to display. The perceptibility of the extraction region can be improved as a result. Incidentally, the other region than the extraction region (hereinafter referred to as the "background region") is displayed in extreme white or black, but this poses no particular problem in image diagnosing.

The gain/dynamic range automatic adjusting means, when a region extracted from one medical image is superposed over an extraction region from the other medical image, automatically so adjusts various parameters as to make the two superposed region clearly perceptible. A number of preset adjusting patterns of the parameters, differentiated by the purpose, may be prepared in advance. The purposes of presetting include the following for instance.

Presetting to match the habits of the user (examiner).
Presetting to match the region in the body (classified by the organ, such as gallbladder, liver, pancreas and so on).
Presetting to match the region of extraction (tumorous region, treated region and so on).

Further, presetting may be made ready according to the conditions of comparison of the extraction region and the background region or the conditions of comparison of the extraction regions taken out of two medical images. The conditions of comparison may include the following for instance.

Presetting for cases in which image signals of the extraction region are hypo-signals compared with (lower signals than) image signals of the background region.
Presetting for cases in which image signals of the extraction region are hyper-signals compared with (higher signals than) image signals of the background region.
Presetting for pathological judgment by comparing the shapes of the contour lines (boundaries) of extraction regions taken out of two medical images.
Presetting to match the internally depicted states of extraction regions taken out of two medical image (textural feeling, such as more rugged or coarse than the surrounding region).

Incidentally, presetting may be made ready according to other conditions than the foregoing.

Figure 9:
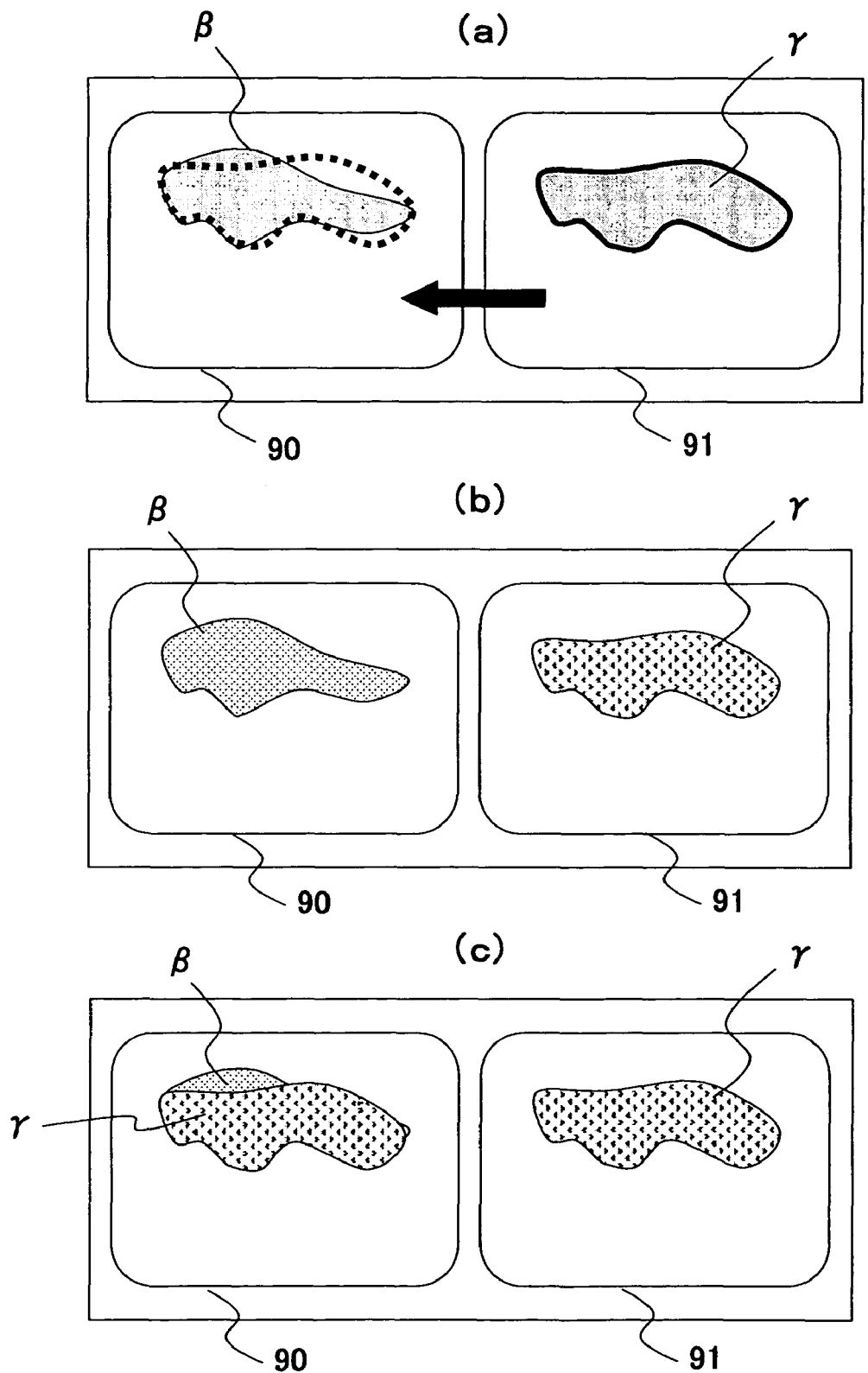
FIG. 9(a) shows a case of utilizing the result of region extraction, a state in which the boundaries of extraction region β and γ are emphatically displayed superposed.
FIG. 9(b) shows a state in which the extraction region β and the extraction region γ are separately displayed with the textures of the extraction region β and the extraction region γ being emphasized.
FIG. 9(c) shows a state in which the extraction region β and the extraction region γ are shown superposed one over the other with the textures of the extraction region β and the extraction region γ being emphasized.

FIGS. 9 show medical images 90 and 91 obtained by imaging the same region of the same object at different times. Similar processing to that in the first embodiment is done to take out an extraction region β from the medical image 90. Similarly an extraction region γ is taken out from the medical image 91.

In FIG. 9(a), the boundary of the extraction region γ is shown superposed over the extraction region P of the medical image 90.

In the way shown in FIG. 9(a), the user selects presetting of (6) above out of the options of gain/dynamic range automatic adjustment, and the extraction region β and the boundary of β are displayed with emphasis. Where the extraction regions β and γ are tumorous regions, the user may select presetting of (3) above. This would make the difference in contour line evident, and this difference reveals the extent of the growth of the cancerous tissue.

In the way shown in FIG. 9(b), the user selects presetting of (7) above to emphasize the textural features of the extraction region P and of the extraction region γ, and displays the extraction region β and the extraction region γ separately (without superposing them). The difference in texture between the two extraction regions is thereby made better perceivable.

In the way shown in FIG. 9(c), the user selects presetting of (7) above to emphasize the textural features of the extraction region β and of the extraction region γ, and displays the extraction region β and the extraction region γ superposed one over the other. The difference not only in texture but also in extraction region size is thereby made better perceivable.

Conventionally, when a plurality of medical images are to be comparatively observed, the gain/dynamic range is manually adjusted to make the noted region better perceivable, but this embodiment makes it possible to automatically obtain the most suitable superposed display images.

Furthermore, in each of medical diagnostic imaging apparatuses displaying the same screen, it is made possible to achieve superposed displaying of not only the desired extraction region but also intrinsic information. Examples include hardness in the extraction region and information to identify the lesioned region.

Figure 13:
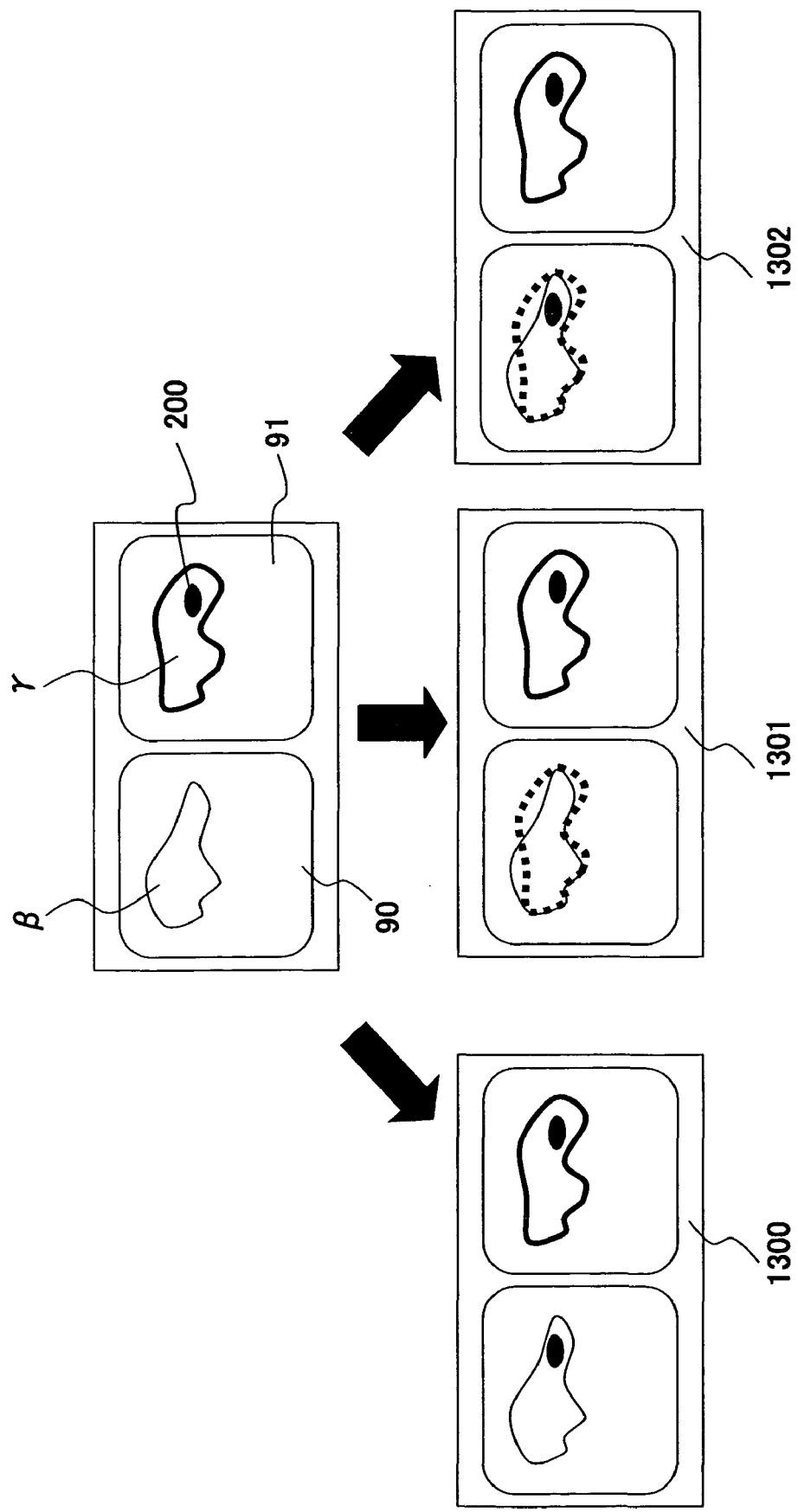
FIG. 13 shows an aspect of superposition where a focus is included in the extraction region γ.

FIG. 13 shows an example of such a case. Medical images 90 and 91 are obtained from different diagnostic apparatuses and displayed on a single screen. It is supposed that the region β is extracted from the medical image 90 and the region γ of the same region as the region β are from the medical image 91. It is further supposed that, for instance, a lesion 200 which cannot be confirmed by the medical image 90 is identified within the extraction region γ of the medical image 91. Means to superpose the two images one over the other is shown on a display screen 1300. It has in combination a method of superposing only the region of the lesion 200 of the medical image 91 over the medical image 90, a method of superposing together the extraction region γ and the lesion 200 of the medical image 91 over the medical image 90 as shown on a display screen 1301, or a method of superposing only the contour of the extraction region as shown on a display screen 1302 similarly to other cases described above.

Although the foregoing description referred only to the superposition of a lesioned region, the applicability is not limited to this, but may also include information on textural hardness degrees in the extraction region distinguished by color.

<Sixth Embodiment>

The sixth embodiment concerns an image diagnosing support system provided with means for realizing a shape measuring function for extraction regions. The shape measuring function may be exercised by the extraction region displaying/measuring unit 9 in the first embodiment, or shape measuring means may be provided in addition to the constituent elements in the first embodiment and the fourth embodiment.

The shape measuring means measures the characteristic quantities of the extraction region including for instance the actually measured square measure (S) and the external circumferential length (L). Further, where there are two extraction regions, it measures the ratio between the characteristic quantities of the two extraction regions, including for instance the square measures (S1/S2) and the longer diameter ratio (L1/L2). It may also measure other items of geometric information and characteristic quantities. When an instruction to execute shape measuring is given in one medical image, automatic measuring of extraction regions is also done in the other medical image.

Figure 10:
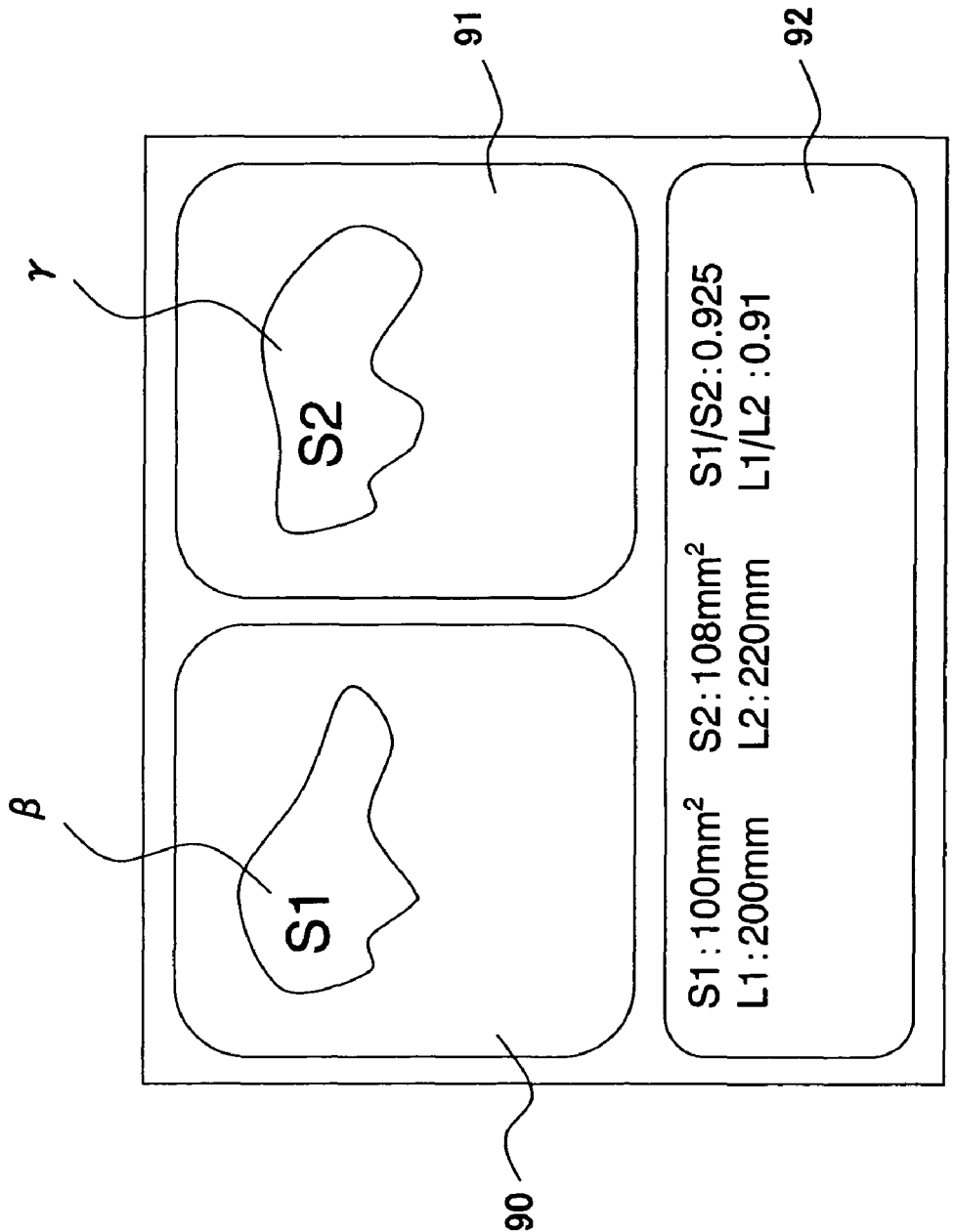
FIG. 10 shows a state in which the result of execution of a shape measuring function is displayed.

For instance in a state of displaying FIG. 9(b), the user designates either the extraction region β or the extraction region γ and instructs execution of the shape measuring function. The means for realizing the shape measuring function (for instance the extraction region displaying/measuring unit 9) calculates the extraction region β, the actually determined square measures S1 and S2 of the extraction region β, the actually measured external circumferential lengths L1 and L2, the square area ratio S1/S2 and the external circumferential length ratio L1/L2. FIG. 10 shows a state in which the results of this calculation are displayed together with the medical images 90 and 91. FIG. 10 shows the extraction region P of the medical image 90, the extraction region γ of the medical image 91 and a display region 92 displaying the result of shape measuring. The result of shape measuring is displayed on the display region 92.

In this embodiment, simultaneous automatic measuring is made possible of the same region contained in a plurality of medical images. This enables diagnosis assisting information to be provided during, for instance, observation of changes in the same patient over time before and after treatment.

<Seventh Embodiment>

In the seventh embodiment, an image diagnosing support system reads in a plurality of medical images picked up by a medical imaging apparatus of the same region of the same object at different times. These medical images contain information on the times of imaging.

And the image diagnosing support system, performing similar processing to that in the foregoing embodiment, extracts the same region from medical images picked up at different times. In this embodiment, the same blood vessel section is extracted. And the image diagnosing support system in this embodiment displays on the same screen time-series images of these extraction regions (the same blood vessel section imaged at different times) displayed along the time series and a hetero-angle image resulting from designation of a random time from those time-series images and displaying the same region at that random time (the time desired by the user) from a different angle. The time-series images are a collection of images of a plurality of time phase images, which represent changes of a blood vessel section over time.

Figure 11:
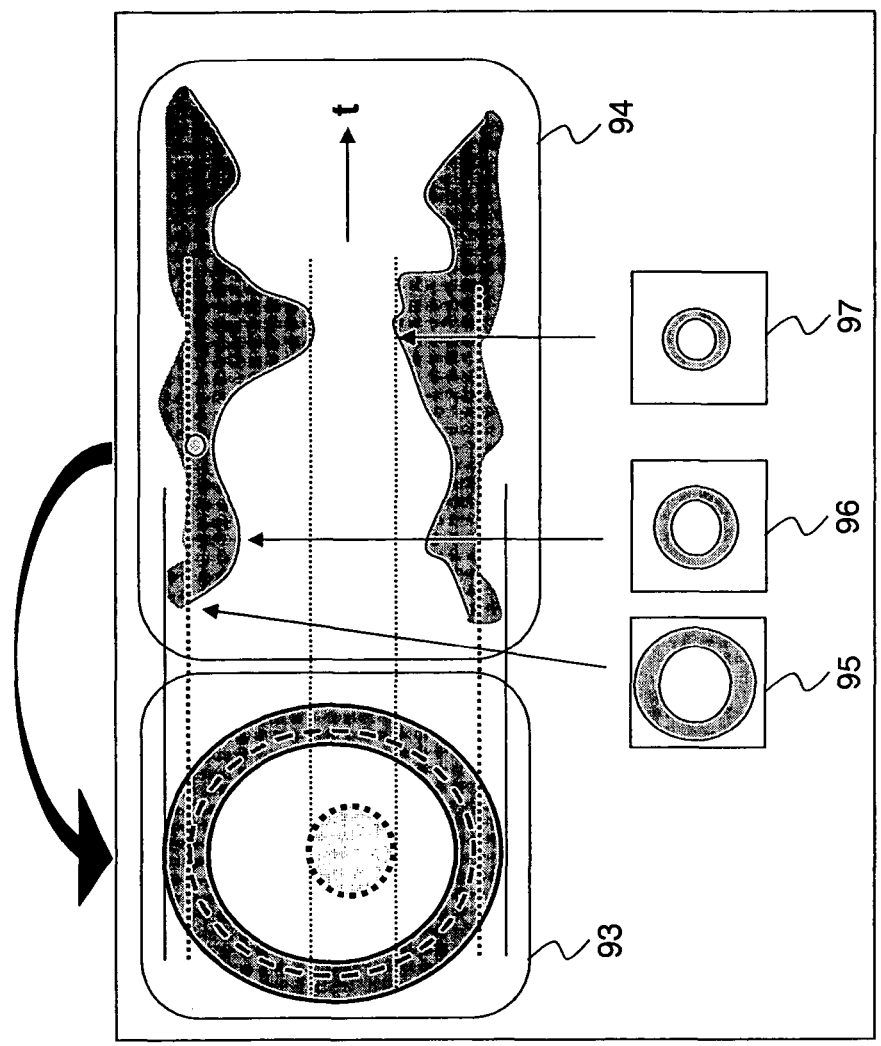
FIG. 11 shows a state in which a hetero-angle image 93 and a time-series image 94 are displayed on a single screen.

FIG. 11 shows a state in which a hetero-angle image 93 and time-series images 94 are displayed on a single screen. The time-series images 94 are images taken of the same region (a section of a blood vessel) at different times and displayed in the direction of the time axis t. The time-series images 94 show that the rate of constriction of a section of the same blood vessel varies over time.

The user selects a random time phase out of the time-series images 94 by using the input unit 6, which may be a mouse or a track ball. Then, the hetero-angle image 93 taken of the same region in that time phase from a different angle is shown. The hetero-angle image 93 may show only the section in the user-designated time phase (the outermost circle in the hetero-angle image 93) or be combined with a section in a later time phase than that time phase (the section indicated by the dotted line). The hetero-angle image 93 can be displayed by reading a medical image out of a cine-memory.

The image diagnosing support system may also display together thumbnail images 95, 96 and 97 of the hetero-angle image matching random time phases of the time-series images 94.

This embodiment enables time-series images comprising a plurality of medical images picked up at different times displayed along the time series and a hetero-angle image matching a random time phase in those time-series images to be displayed on the same screen, and can thereby contribute to improving diagnostic capabilities.

Industrial Applicability

This can be applied to not only displaying of a medical image but also to uses wherein, when a plurality of images taken of the same object (or object of imaging) are to be displayed in parallel, processing to extract a region from one of the images results in extraction of a matching region in another image. It is also applicable to, besides measuring the rates of constriction of blood vessels, measuring the rates of constriction of other tubule organs or tubule objects of imaging.

The invention claimed is:

1. An image diagnosing support method comprising:
acquiring a plurality of images obtained by imaging a same region of a same object with one or more medical imaging apparatuses;
selecting a first image from a first medical imaging apparatus and a second image from another medical imaging apparatus, the first and second images registering a common spatial position of a magnetic sensor, as an alignment reference;
simultaneously displaying said first image and said second image in the same section of the object;
designating one or more of first reference points in an extraction region desired by a user, on said first image;
extracting a first region on said first image on a basis of each of said first reference point and the brightness information on said first image;
automatically designating one or more second reference points on said second image, matching said one or more first reference points, on the basis of the positional information of said first reference points on the first image; and
extracting a second region on said second image on a basis of each of said second reference point and the brightness information on said second image;
wherein the boundary of a region extracted from said first image and the boundary of a region extracted from said second image and said second reference point, are displayed superposed over said second image, and the boundary of a region extracted from said second image and the boundary of a region extracted from said first image and said first reference point, are displayed superposed over said first image, and
automatically adjusting gain and dynamic image parameters so as to match the distribution range of image signal values in the extraction region with maximum gradation range of image displaying to display.

2. The image diagnosing support method according to claim 1, further comprising displaying region information on at least one of said first region and said second region superposed over at least one of said first image and said second image.

3. The image diagnosing support method according to claim 2, wherein:
the extraction of said first region and said second region is accomplished by successively comparing pixel values in the vicinities of said reference points with a prescribed threshold.

4. The image diagnosing support method according to claim 2, wherein:
said region information is information representing at least one of the whole extracted region and the boundary thereof.

5. The image diagnosing support method according to claim 2, further comprising acquiring geometric information that at least either said first region or said second region has.

6. The image diagnosing support method according to claim 5, wherein:
said first image and said second image are images obtained by picking up a same blood vessel of said object and contains a vascular sectional region including a luminal region in which blood flows and a vascular tissue region, said luminal region and said vascular tissue region are respectively extracted and, the method further comprising:
- extracting a plurality of parameters necessary for figuring out the rate of constriction of said blood vessel from at least one of said luminal region and said vascular tissue region, and
- deriving the rate of constriction of said blood vessel by using said plurality of parameters.

7. The image diagnosing support method according to claim 6, wherein:
said plurality of parameters include at least either the internal diameter of said luminal region and the external diameter of said vascular tissue region, or the square measure of said luminal region and the square measure of said vascular tissue region.

8. The image diagnosing support method according to claim 1, wherein:
said first image and said second image are images picked up by medical imaging apparatuses of different types.

9. The image diagnosing support method according to claim 8, wherein:
at least one of said first image and said second image is an image picked up by a medical imaging apparatus capable of real-time imaging.

10. The image diagnosing support method according to claim 1, wherein:
said first image and said second image are images picked up by different medical imaging apparatuses of the same type.

11. The image diagnosing support method according to claim 10, wherein:
at least one of said first image and said second image is an image picked up by a medical imaging apparatus capable of real-time imaging.

12. The image diagnosing support method according to claim 1, wherein:
said first image and said second image are images picked up by the same medical imaging apparatus.

13. The image diagnosing support method according to claim 12, wherein:
at least one of said first image and said second image is an image picked up by a medical imaging apparatus capable of real-time imaging.

14. The image diagnosing support method according to claim 1, wherein:
said first image and said second image are images of the same section of the object.

15. The image diagnosing support method according to claim 1, wherein:
said first image and said second image are images of different sections of the same region of said object.

16. The image diagnosing support method according to claim 1, wherein:
said first image and said second image are images picked up at different times.

17. The image diagnosing support method according to claim 1, wherein:
said plurality of images further have time information on the times of being picked up,
said first image is an image representing changes of said region, and
said second image is an image of said region of said first image, at a desired point of time.

18. The image diagnosing support method according to claim 1, wherein said first image is generated by an x-ray CT apparatus or a MRI apparatus, and said second image is generated by an ultrasonic imaging apparatus.

19. An image diagnosing support apparatus comprising:
an acquiring unit configured to acquire a plurality of images obtained by imaging a same region of a same object with one or more medical imaging apparatuses;
a selecting unit configured to effect selecting of two or more images out of said plurality of images, at least two of the images being obtained by different medical imaging apparatuses, the at least two or more images registering a common spatial position of a magnetic sensor, as an alignment reference
a display unit configured to display said selected two or more images in a same section of the object;
a designating unit configured to designate one or more of first reference points in an extraction region desired by a user, on one of said selected two or more images;
a first-region extracting unit configured to extract a first region on said first image, on the basis of each of said first reference point and the brightness information on said first image;
an automatic designating unit configured to automatically designate one or more second reference points on said second image matching said one or more first reference points, on the basis of the positional information of said first reference points on the first image;
a second-region extracting unit configured to extract a second region on said second image, on the basis of each of said second reference point and the brightness information on said second image;
wherein the boundary of a region extracted from said first image and the boundary of a region extracted from said second image and said second reference point, are superposed over said second image, and the boundary of a region extracted from said second image and the boundary of a region extracted from said first image and said first reference point, are displayed superposed over said first image, and
wherein gain and dynamic image parameters are automatically adjusted so as to match the distribution range of image signal values in the extraction region with maximum gradation range of image displaying to display.

20. The image diagnosing support apparatus according to claim 19, further comprising a region-display unit configured to display region information on at least either said first region or said second region superposed over at least either one of said selected two or more images.

21. An image diagnosing support apparatus comprising:
a selecting unit configured to effect selecting of two or more images out of a plurality of images obtained by imaging a same region of a same object fitted with a registration arrangement causing registration of a common spatial position of the object within each of the plurality of images, the two or more images being obtained by different medical imaging apparatuses;
a display unit configured to display the two or more images in the same region of the object;
a designating unit configured to designate one or more of first reference points in an extraction region desired by a user, on one of the two or more images as a first image;
a first-region extracting unit configured to extract a first region on the first image, on a basis of each of the one or more first reference points, and brightness information, of the first image;

an automatic designating unit configured to automatically designate one or more second reference points on a second image of the two or more images, on a basis of the registration of the common spatial position on the first and second images, and the positional information of the first reference points on the first image, the one or more second references points spatially matching the one or more first reference points;

a second-region extracting unit configured to extract a second region on the second image, on a basis of each of the second reference point, and the brightness information, of the second image;

wherein at least one of: the boundary of a region extracted from the first image is displayed superposed over the second image; and the boundary of a region extracted from the second image is displayed superposed over the first image, and wherein gain and dynamic image parameters are automatically adjusted so as to match the distribution range of image signal values in the extraction region with maximum gradation range of image displaying to display.

22. The image diagnosing support apparatus according to claim 21, wherein the registration arrangement is one of: a magnet and a probe, provided to the object.

* * * * *